United States Patent
Kerner

(10) Patent No.: US 6,567,156 B1
(45) Date of Patent: May 20, 2003

(54) APPARATUS AND METHOD FOR EXAMINING THE SHAPE OF GEMSTONES

(75) Inventor: Abraham Kerner, Herzeliah (IL)

(73) Assignee: Sarin Technologies Ltd., Ramat-Gan (IL)

( * ) Notice: Subject to any disclaimer, the term of this patent is extended or adjusted under 35 U.S.C. 154(b) by 287 days.

(21) Appl. No.: 09/652,465

(22) Filed: Aug. 31, 2000

(51) Int. Cl.$^7$ .................. G01N 21/00; G01B 11/24; G01B 11/30

(52) U.S. Cl. .................. 356/30; 356/601; 356/602; 356/603; 356/613

(58) Field of Search .................. 356/30, 394, 399, 356/601–603, 613; 125/30 R; 51/165.72

(56) References Cited

U.S. PATENT DOCUMENTS

| | | | | |
|---|---|---|---|---|
| 4,302,097 A | | 11/1981 | Chlestil | 355/52 |
| 4,406,544 A | | 9/1983 | Takada et al. | 356/376 |
| 4,417,564 A | | 11/1983 | Lawrence et al. | 125/30 |
| 4,529,305 A | * | 7/1985 | Welford et al. | 356/30 |
| 4,629,319 A | | 12/1986 | Clarke et al. | 356/237 |
| 4,764,401 A | * | 8/1988 | Sirinyan et al. | 427/304 |
| 4,863,268 A | | 9/1989 | Clarke et al. | 356/237 |
| 4,892,857 A | * | 1/1990 | Tennent et al. | 428/469 |
| 4,907,888 A | | 3/1990 | Clarke et al. | 356/371 |
| 5,075,204 A | * | 12/1991 | Shiba et al. | 430/496 |
| 5,076,698 A | * | 12/1991 | Smith et al. | 356/30 |
| 5,230,924 A | * | 7/1993 | Li | 228/124.1 |
| 5,283,642 A | | 2/1994 | Sarr | 348/133 |
| 5,365,364 A | * | 11/1994 | Taylor | 347/256 |
| 5,753,931 A | | 5/1998 | Borchers et al. | 250/559.22 |
| 6,020,954 A | * | 2/2000 | Aggarwal | 356/30 |
| 6,111,699 A | * | 8/2000 | Iwata et al. | 359/599 |
| 6,134,342 A | * | 10/2000 | Doke et al. | 356/124 |
| 6,239,867 B1 | * | 5/2001 | Aggarwal | 356/30 |
| 6,418,254 B1 | * | 7/2002 | Shikata et al. | 385/115 |
| 2001/0023925 A1 | * | 9/2001 | Smith | 250/372 |
| 2002/0014577 A1 | * | 2/2002 | Ulrich et al. | 250/205 |

FOREIGN PATENT DOCUMENTS

| | | | | |
|---|---|---|---|---|
| EP | 872 708 | | 10/1998 | |
| GB | 2081439 A | * | 2/1982 | G01N/21/87 |
| IL | 66292 | | 7/1982 | |
| JP | 02257007 A | * | 10/1990 | G01B/11/30 |
| JP | 403274180 A | * | 12/1991 | 503/214 |
| JP | 04305144 A | * | 10/1992 | G01N/21/84 |
| JP | 04321186 A | * | 11/1992 | G06F/15/62 |

* cited by examiner

Primary Examiner—John R. Lee
Assistant Examiner—Bernard Souw
(74) Attorney, Agent, or Firm—Abelman, Frayne & Schwab

(57) ABSTRACT

A method for examining a gemstone includes the steps of coating the gemstone with a removable diffusing coating and determining the silhouette of the gemstone in three dimensions. The method further includes performing structured light triangulation by using laser light to obtain an image of the surface of the gemstone, the gemstone being transparent and/or reflective to the laser light in the absence of the coating. The method further includes the step of using the silhouette in conjunction with the image to determine the location of any recesses on the surface.

14 Claims, 2 Drawing Sheets

APPARATUS AND METHOD FOR EXAMINING THE SHAPE OF GEMSTONES

BACKGROUND OF THE INVENTION

Due to the high cost of gemstones and diamonds and the work involved in finishing them, it is desirable to determine, in advance, the optimal finished stone which can be cut from an uncut gemstone or diamond. In the past, this was done by eye by the individual who would work the gemstone or diamond, particularly in the case of a diamond. If an error was made, either more material than necessary was removed and wasted, or the entire stone had to be discarded.

Accordingly, with the increasing use of computers, a number of computerized systems were developed for examining gemstones and diamonds, and comparing the shape of the stone with a variety of pre-selected shapes in order to determine which is the best fit. This is generally accomplished by mounting the stone on a rotating dop or other holder, and scanning the rotating stone. According to one series of patents, the stone is lit from the rear, providing a silhouette of the stone, which is analyzed by the computer and compared with a number of silhouettes of finished stones. According to another series of patents, such as U.S. Pat. No. 4,417,564, the stone is scanned normal to the axis, so as to permit the computer to provide a three-dimensional image of the stone.

One particular problem which is not solved by conventional devices, especially those analyzing a silhouette, is the case of a reentrant or recess in the stone. While it is clear that any protrusions will be visible in the silhouette, a recess will not be visible, which results in many incorrect decisions regarding the proper working of stones.

One patent which purports to solve this problem is Israel Patent 66292 to Gersan Establishment. This patent describes a method of examining a gemstone which includes projecting a thin beam of light onto the stone, moving the beam relative to the stone, sensing the position where the beam strikes the stone, as viewed in a direction different from that in which the beam is projected, and determining a parameter of the stone making use of information derived from sensing that position. This patent suffers from a number of disadvantages. First, a thin beam of light is not sufficiently precise to provide accurate measurement of reentrants. Second, and more important, since most gemstones and diamonds are transparent and reflective, the beam of light will not be reflected in a way that it can be viewed by a camera which is located as illustrated in this patent.

Similarly, when three dimensional objects are to be scanned or measured, it is either difficult or very expensive to measure depressions or recesses in the surface of the object.

There is known a method of measuring distance known as structured light triangulation which is based on a laser as the light source. This method is used for robotic and computer vision systems. This method is not suitable for mapping the surface of a gemstone or diamond since their surfaces are either transparent or reflective and, thus, cannot be viewed by a camera.

Accordingly, there is a long felt need for an apparatus and method for examining an object, particularly a gemstone, which can rapidly and inexpensively provide a 3-dimensional image of the object, including mapping recesses and reentrants in the object.

SUMMARY OF THE INVENTION

According to the present invention, there is provided a method for examining an object including the steps of coating the object with a diffusing coating, determining the silhouette of the object in three dimensions, and using structured light triangulation to determine the location of any recesses in the surface of the object.

According to a preferred embodiment, the method includes the steps of coating the object with a diffusing coating, mounting the object on a rotating holder, illuminating the object from behind to create a silhouette, illuminating a line or grid on the object, preferably by means of a laser, scanning the object by means of a camera disposed in front of the object and at a predefined acute angle from the laser for, providing signals from the camera corresponding to the shape of the object, and generating an image of the object from the signals.

According to one embodiment of the invention, the step of coating includes electrochemical electro-less coating of the object.

According to another embodiment of the invention, the step of coating includes painting the object with a layer of between about 10 and 20 microns of paint.

According to yet another embodiment of the invention, the step of coating includes vacuum evacuation.

According to one embodiment of the invention, the steps of illuminating the object from behind and illuminating the object by means of a laser are carried out substantially simultaneously.

According to an alternative embodiment of the invention, the step of illuminating the object from behind is carried out before the step of illuminating the object by means of a laser.

There is also provided in accordance with the present invention an apparatus for examining a object including means for holding a object coated with a diffusing material, a first light source for illuminating the object from behind to create a silhouette, a second light source for illuminating a line or grid on the object, a camera disposed in front of the object and at a predefined acute angle from the second light source for scanning the object and providing signals corresponding to the shape of the object, and a processor for generating an image of the object from the signals.

BRIEF DESCRIPTION OF THE DRAWINGS

The present invention will be further understood and appreciated from the following detailed description taken in conjunction with the drawings in which.

DETAILED DESCRIPTION OF THE INVENTION

The present invention relates to an apparatus and method for examining an object which provides rapid and accurate assessment of the shape of the object. The invention is particularly useful for examining a gemstone, in order to provide a so-called fingerprint of the stone, or in order to determine the optimal final shape of an unfinished stone, although it is not limited to this use. The invention accomplishes its goal by combining two technologies to provide overlapping information about the three-dimensional shape of the stone, namely scanning the silhouette of a stone to determine the overall shape in three dimensions, and structured light triangulation to add the location of any recesses or reentrants in the surface of the gemstone to the generated image of the stone.

For ease of discussion, the invention will be described hereinbelow with regard to examining a gemstone, although it will be appreciated that the description is substantially the same for examination of other three-dimensional objects. Thus, for purposes of the present application, the term "gemstone", or "stone", will be used to include any precious or semi-precious gemstone, an uncut stone, a partially worked stone, a finished stone, and any other three-dimensional object for which an accurate image of the surface is required.

Figure 1:
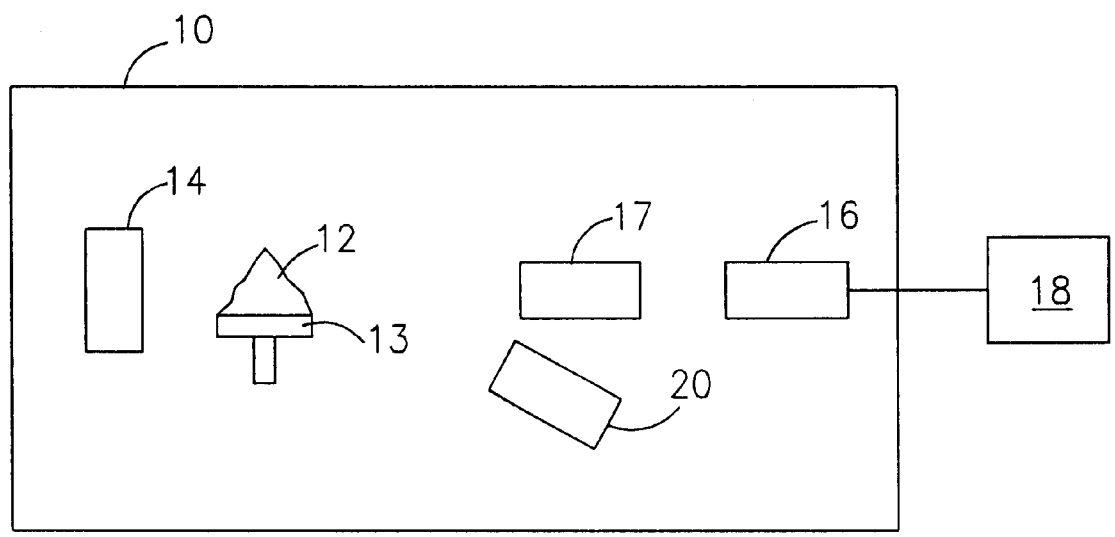
FIG. 1 is a schematic illustration of an apparatus for examining a gemstone constructed and operative in accordance with one embodiment of the invention.

Referring now to FIG. 1, there is shown a schematic illustration of an apparatus 10 for examining a gemstone constructed and operative in accordance with one embodiment of the invention. Apparatus 10 includes a gemstone 12 mounted on a rotating holder or dop 13, as known. A source 14 of light is provided to back light the stone. Scanning apparatus 16 for scanning the stone, preferably a CCD camera, is provided in front of the stone, for detecting the silhouette of the stone. Suitable optical imaging lenses 17 are provided between gemstone 12 and scanning apparatus 16. Scanning apparatus 16 is coupled to a processor 18 which processes signals from scanning apparatus 16 corresponding to the shape of the gemstone 12, and generates therefrom a 3-dimensional image of the gemstone, all as known.

Apparatus 10 also includes a light source 20, preferably a source of laser light. Light source 20 is mounted in front of gemstone 12 and at a pre-selected acute angle, relative to the stone, from scanning apparatus 16. In this fashion, laser light reflected from gemstone 12 is detected by scanning apparatus 16.

Operation of the apparatus of the invention is as follows. A gemstone to be examined is selected. The gemstone is coated with a removable diffusing coating to permit the scanning apparatus to detect laser light reflected from the surface thereof. It will be appreciated that, at present, a diffusing coating is required for all objects which are transparent or reflective, so as to provide diffusion of the light impinging thereon, and permit detection by the triangulation scanner. Alternatively, if a light source is utilized which has a wavelength to which the object is not transparent or reflective, there is no need for a coating.

The coating is preferably on the order of 5–15 microns in depth, or less, since the precision of the overall apparatus is 10 microns. It will be appreciated that without a diffusing coating, the gemstone cannot be mapped using structured light with conventional light sources. On the other hand, coating gemstones, particularly diamonds, is problematic, since few materials adhere to the surface.

Three possible methods of coating the stone are as follows. It will be appreciated, however, that these methods are provided solely by way of example, and the invention also includes any other method of coating a gemstone with a diffusing coating. The first method includes electro-less electrochemical coating, in which the surface tension of the stone is utilized to adhere a thin coating of a liquid onto the surface of the stone, without an electric current.

The second method includes submerging the stone in paint and drying the stone in a very rapid air flow, which blows off all but a thin layer of paint. The third method is vacuum evaporation, such as used today for coating optical lenses. According to this method, a coating liquid is placed next to the stone in a vacuum chamber. Under vacuum, the liquid evaporates and then adheres to the stone.

The coated stone is then placed on a rotating holder. Alternatively, the light sources and camera can rotate around the stone, but the apparatus is simpler if only the stone rotates. As the gemstone 12 rotates, the stone is illuminated from the rear by light source 14. Scanning apparatus 16 views the stone, and detects its silhouette. Signals corresponding to the silhouette are sent to processor 18, which generates a 3-dimensional image of the stone from the signals.

Figure 2:
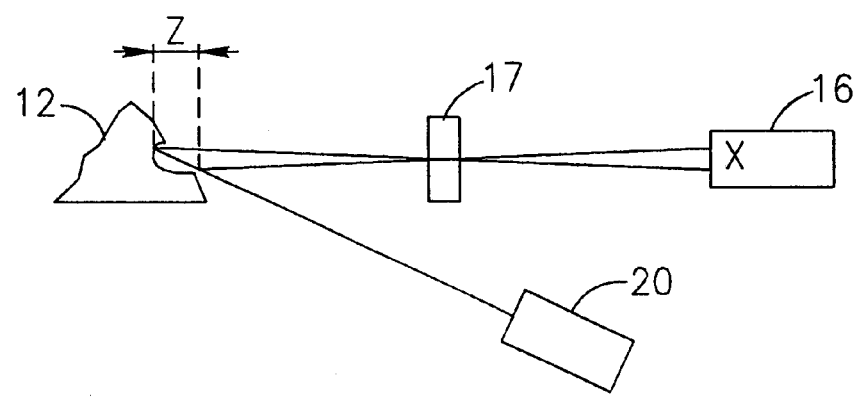
FIG. 2 is a schematic illustration of the use of structured light triangulation in the invention.

After the image is generated, or substantially simultaneously with detecting the silhouette, or alternating with detecting the silhouette, light source 20 illuminates a point, line or grid on the stone. Alternatively, light source 20 can simultaneously illuminate several lines, or several light sources can simultaneously illuminate the stone. If the stone has a convex surface, the light will be reflected and coincide with a corresponding point on the silhouette. However, if the stone has a concave surface at one point, the light will be reflected to a different location on the image of the stone. The angle between the camera and the light source causes the image to appear at different places when the object is at different ranges. Utilizing principles of triangulation, the distance from the reference point to the reflecting point on the surface of the stone can be calculated from the known distance and angle between the camera and the light source. Thus, as the distance from the camera to the surface of the stone changes by z, the light reflected from the surface is imaged to a new position on the detector, moved by a distance x, as shown schematically in FIG. 2.

Figure 3:
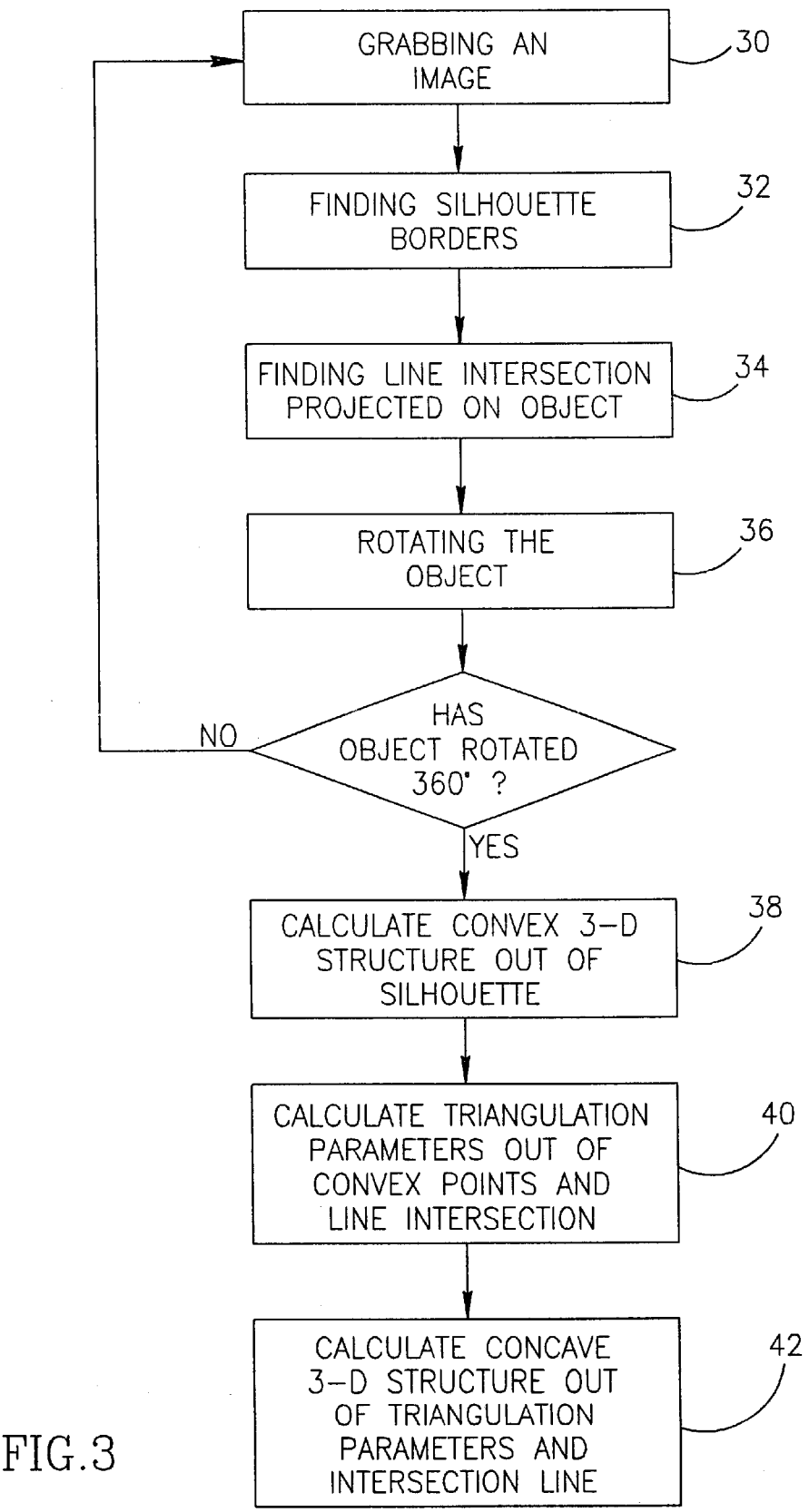
FIG. 3 is a flow chart of the operation of the processor in the apparatus of the invention.

The video out of the scanning apparatus is connected to a frame grabber. For each line scan, there is a correspondence between the distance to the object, and the position of the object line in the camera view. This correspondence is defined by triangulation. The signal processing software finds the position of this line as a set of data points. When these data points are superimposed on the silhouette of the stone, the generated image includes an indication of the location, curvature, and depth of any recess on the surface of the stone. A flow chart of the operation of processor 18 is shown in FIG. 3. As can be seen, the processor begins by grabbing an image from the scanning apparatus (block 30). The image processor determines the silhouette borders (block 32). The processor also finds the line intersection projected onto the stone (block 34). The stone is now rotated incrementally (block 36), and the steps of blocks 30, 32, 34, and 36 are repeated. The stone continues to be rotated incrementally until it has rotated through 360°, and the entire silhouette has been mapped.

The convex three-dimensional structure of the silhouette is now calculated (block 38). Triangulation parameters are calculated from the convex points and line intersection (block 40), unless they were calculated in advance rather than on-line during the measuring process, and the processor calculates the concave three-dimensional structure from the triangulation parameters and the intersection line (block 42). This process permits accurate mapping also of those portions of the surface of the object which cannot be seen in a silhouette.

The apparatus and method according to the invention provide several advantages over conventional systems. First, the accurate mapping of the surface of a gemstone is much faster, utilizing the combination of two technologies. Second, on-line calibration of triangulation parameters is possible using the two methods substantially simultaneously, permitting measurement of the distance from the shadow edge to the laser light. For example, the camera can detect the silhouette during one quarter rotation, followed by one quarter rotation for detecting structured light, etc. In fact, any object can be utilized for calibration of the triangulation parameters.

According to a preferred embodiment of the invention, the apparatus for examining a gemstone is a small, easily portable device. Thus, it can be utilized for examining gemstones after any stage of processing—uncut gemstones, partially worked gemstones, or even finished gemstones, when it is desired to uniquely identify a particular stone. It is also convenient for use in any other setting where a three-dimensional object is to be mapped.

It will be appreciated that the invention is not limited to what has been described hereinabove merely by way of example. Rather, the invention is limited solely by the claims which follow.

What is claimed is:

1. A method for examining a gemstone comprising the steps of:
    (a) coating said gemstone with a removable diffusing coating;
    (b) determining the silhouette of said gemstone in three dimensions;
    (c) performing structured light triangulation by using laser light to obtain an image of the surface of said gemstone, said gemstone being transparent and/or reflective to said laser light in the absence of said coating; and
    (d) using said silhouette in conjunction with said image to determine the location of any recesses on said surface.

2. The method according to claim 1, further comprising the step of utilizing said silhouette and said location to generate an image of the gemstone, including the location of any recesses on the surface of the gemstone, said image being suitable to uniquely identify the gemstone or, if the gemstone is unfinished, for determining the optimum finished stone which can be obtained therefrom.

3. The method according to claim 1, wherein:
    said step (b) includes illuminating the gemstone from behind; and
    said illuminating and said step (c) are carried out substantially simultaneously.

4. The method according to claim 2, wherein:
    said step (b) includes illuminating the gemstone from behind; and
    said illuminating and said step (c) are carried out substantially simultaneously.

5. The method according to claim 1, wherein:
    said step (b) includes illuminating the gemstone from behind; and
    said illuminating is carried out before step (c).

6. The method according to claim 2, wherein:
    said step (b) includes illuminating the gemstone from behind; and
    said illuminating is carried out before step (c).

7. The method according to claim 1, further comprising the step of mounting the gemstone on a rotating holder, wherein:

said step (b) includes illuminating the gemstone from behind by means of a first light source to create said silhouette;
    said step (c) includes illuminating a point, line, or grid on the gemstone by means of a laser light source;
    said steps (b) and (c) include scanning the gemstone by means of a camera disposed in front of the gemstone and at a predefined acute angle from said second light source and obtaining thereby signals from the camera; and
    said step (d) includes generating an image of the gemstone which includes said recesses, if any, from said signals, said image being suitable to uniquely identify the gemstone or, if the gemstone is unfinished, for determining the optimum finished stone which can be obtained therefrom.

8. The method according to claim 1, wherein said step (a) includes electrochemical electro-less coating of the gemstone.

9. The method according to claim 1, wherein said step (a) includes painting the gemstone with a layer of between about 5 and 15 microns of paint.

10. The method according to claim 1, wherein said step (a) includes vacuum evaporation.

11. The method according to claim 1, wherein said steps (b) and (c) are performed simultaneously.

12. The method according to claim 1, wherein said step (b) is performed before step (c).

13. An apparatus for examining a gemstone coated with a diffusing material by generating an image of the gemstone including the location of any recesses on the surface thereof, said image being suitable to uniquely identify the gemstone or, if the gemstone is unfinished, for determining the optimum finished stone which can be obtained therefrom, said apparatus comprising:
    means for holding the coated gemstone;
    a first light source for illuminating the gemstone from behind to create a silhouette;
    a second light source in the form of a laser for illuminating a point, line or grid on the gemstone to perform structured light triangulation, said second light source being such that said image can be obtained using said structured light triangulation only with said gemstone being coated with said material;
    a camera disposed in front of the gemstone and at a predefined acute angle from the second light source for scanning the gemstone, thereby obtaining signals corresponding to the shape of the gemstone; and
    a processor for generating said image of the gemstone from said signals by using said light triangulation in conjunction with said silhouette in order to determine the location of any recesses on the surface of the gemstone.

14. The apparatus according to claim 13, wherein:
    said first light source and said camera are located on a common axis; and
    said means for holding the gemstone are disposed on said axis, between said first light source and said camera.

* * * * *